(12) United States Patent
Doyle et al.

(10) Patent No.: US 7,947,487 B2
(45) Date of Patent: *May 24, 2011

(54) MULTIFUNCTIONAL ENCODED PARTICLES FOR HIGH-THROUGHPUT ANALYSIS

(75) Inventors: Patrick S. Doyle, Boston, MA (US); Daniel C. Pregibon, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 417 days.

This patent is subject to a terminal disclaimer.

(21) Appl. No.: 11/867,217

(22) Filed: Oct. 4, 2007

(65) Prior Publication Data

US 2008/0176216 A1   Jul. 24, 2008

Related U.S. Application Data

(60) Provisional application No. 60/849,651, filed on Oct. 5, 2006.

(51) Int. Cl.
*C12M 1/00* (2006.01)
*C07H 21/04* (2006.01)

(52) U.S. Cl. .......... 435/283.1; 422/68.1; 977/704; 977/712; 977/733; 977/795

(58) Field of Classification Search .......... None
See application file for complete search history.

(56) References Cited

U.S. PATENT DOCUMENTS

| 5,668,268 | A | * | 9/1997 | Tang et al. | 536/25.3 |
|---|---|---|---|---|---|
| 2006/0201390 | A1 | * | 9/2006 | Lahann et al. | 106/401 |
| 2007/0105972 | A1 | | 5/2007 | Doyle et al. | |
| 2008/0213912 | A1 | | 9/2008 | Randall et al. | |

FOREIGN PATENT DOCUMENTS

| WO | WO-2007/050704 A2 | 5/2007 |
|---|---|---|
| WO | WO-2007/075894 A2 | 7/2007 |
| WO | WO-2008/124423 A2 | 10/2008 |

OTHER PUBLICATIONS

Roh et al "Biphasic janus particles with nanoscale anisotropy" Natuer Materials, Oct. 2005, 4: 759-763.*
Nie et al "Janus and ternanry particles generated by microfluidic synthesis: Design, syntheis and self-assembly" J. Am. Chem. Soc. Jul. 2006, 128: 9408-9412.*
Beebe et al "Functional hydrogel structures for autonomous flow control inside microfluidic channels" Nature, 200, 404: 588-590.*
Gershon, D., *Nature* 416, 885, (2002).
Fodor, S. P. et al., *Nature* 364, 555 (1993).
MacBeath, G. and S.L. Schreiber, *Science* 289, 1760 (2000).
Fulton, R.J. et al., *Clin. Chem* 43, 1749 (1997).
Battersby, B.J. et al., *J. Am. Chem. Soc.* 122, 2138 (2000).
Xu, H. et al., *Nucleic Acids Res.* 31, e43 (2003).
Han, M. et al., *Nat Biotechnol.* 19, 631 (2001).

(Continued)

*Primary Examiner* — BJ Forman
(74) *Attorney, Agent, or Firm* — Choate, Hall & Stewart LLP; Fangli Chen

(57) ABSTRACT

Method for making multifunctional particles. The method includes flowing a first monomer stream loaded with a fluorescent entity along a microfluidic channel and flowing a second monomer stream loaded with a probe adjacent to the first monomer stream along the microfluidic channel. The monomer streams are polymerized to synthesize particles having a fluorescent, graphically encoded region and a probe-loaded region.

26 Claims, 11 Drawing Sheets

OTHER PUBLICATIONS

Zhao, X.W. et al., *Chem. Mater.* 18, 2443 (2006).
Cunin, F. et al., *Nat. Mater.* 1, 39 (2002).
Su, X. et al., *Nano Lett.* 5, 49 (2005).
Fenniri, S. et al., *J. Am. Chem. Soc.* 125, 10546 (2003).
Nicewarner-Pena et al., *Science* 294, 137 (2001).
Sha, M. Y. et al., *Anal Bioanal. Chem.* 384, 658 (2006).
Evans, M. et al., *Assay Drug Dev. Technol.* 1, 199 (2003).
Zhi, Z. L. et al., *Anal Chem.* 75, 4125 (2003).
Braeckmans, K. et al., *Nat. Matter* 2, 169 (2003).
Moran, E. J. et al., *J. Am. Chem. Soc.* 117, 10787 (1995).
Nicolaou, K. C. et al., *Agnew, Chem. Int. Ed.* 34, 2289 (1995).
McHugh, T. M. et al., *J. Clin. Microbial* 26, 1957 (1988).
Vaino, A. R. et al., *Natl. Acad. Sc. U.S.A.* 97, 7692 (2000).
Nolan, J.P. et al., *Trends Biotechnol.* 20, 9 (2002).
Fan, J.B. et al., *Nat. Rev. Genet.* 7, 632 (2006).
Ferguson, J. A. et al., *Anal Chem.* 72, 5618 (2000).
Finkel, N.H. et al., *Anal Chem.* 76, 353A (2004).
Braeckmans, K. et al., *Nat. Rev. Drug Discov.* 1, 447 (2002).
Dendukuri, D. et al., *Nat. Mater.* 5, 365 (2006).
Hergt, R. et al., *IEEE Trans. Magn.* 34, 3745 (1998).
Rubina, A. Y. et al., *Biotechniques* 34, 1008 (2003).
Vasiliskov, A. V. et al., *Biotechniques* 27, 592 (1999).
Rehman, F. N. et al., *Nucleic Acids Res.* 27, 649 (1999).
Pregibon, D. C. et al., *Langmuir* 22, 5122 (2006).
Mellott, M. B., *Biomaterials* 22, 929 (2001).
Cruise, G. M. et al., *Biomaterials* 19, 1287 (1998).
Kohara, Y. et al., *Nucleic Acids Res.* 30, e87 (2002).
Simonnet, C. et al., *Anal. Chem.* 78, 5653 (2006).
De Jager, W. et al., *Methods* 38, 294 (2006).
Stevens, P. W. et al., *Nucleic Acids Res.* 27, 1719 (1999).
Irizarry, R. A. et al., *Bioinformatics* 22, 789 (2006).
Dunbar, S. A. et al., *J. Microbiol. Methods* 53, 245 (2003).
Wang et al., *Lab Chip*, 4, 625 (2004).
McClain et al., *Anal. Chem.*, 75, 5646 (2003).
Eyal and Quake, *Electrophoresis*, 23, 2653 (2002).
Sinclair et al., *App. Optics*, 43, 2079 (2004).
Service, R. F., *Science* 270, 577 (1995).
International Search Report from PCT/US2007/080426, mailed Sep. 30, 2008.
Written Opinion of the International Searching Authority, from PCT/US2007/080426, dated Sep. 30, 2008.
Armstrong, B. et al., *Cytometry*, 40, No. 2, 102-108 (2000).
Braeckmans, Kevin et al., *Nature Materials*, 2, No. 3, 169 (2003).
Pregibon, Daniel C. et al., *Science*, 315, 1393 (2007).
Pearce, Megan, E. et al., *Pharmaceutical Research*, 24, No. 12, 2335 (2007).
Hunt, Hamish, C. et al., *Microfluidics and Nanofluidics*, 4, No. 1-2, 53-79 (2008).

\* cited by examiner

▨ Orientation Indicators
☐ Coding Benefits
▦ Analyze Detection Region
↔ Reading Lanes

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 1
atagcagatc agcagccaga                                               20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide probe

<400> SEQUENCE: 2
cactatgcgc aggttctcat                                               20

<210> SEQ ID NO 3
<211> LENGTH: 17
<212> TYPE: DNA
<213> ORGANISM: Artificial Sequence
<220> FEATURE:
<223> OTHER INFORMATION: Oligomer probes

<400> SEQUENCE: 3
gcagatcagc agccaga                                                  17

<210> SEQ ID NO 4
<211> LENGTH: 20
<212> TYPE: DNA
<213> ORGANISM: Artificial Sequence
<220> FEATURE:
<223> OTHER INFORMATION: Oligomer probes

<400> SEQUENCE: 4
cactatgcgc aggttctcat                                               20

MULTIFUNCTIONAL ENCODED PARTICLES FOR HIGH-THROUGHPUT ANALYSIS

This application claims priority to Provisional Application Ser. No. 60/849,651 filed on Oct. 5, 2006, the contents of which are incorporated herein by reference.

GOVERNMENT SUPPORT

This invention was made with government support under grant number CTS0304128 awarded by the National Science Foundation. The government has certain rights in this invention.

BACKGROUND OF THE INVENTION

This invention relates to high-throughput biomolecule analysis and more particularly to a system that utilizes multifunctional encoded particles.

The ability to quantify multiple proteins, cytokines, or nucleic acid sequences in parallel using a single sample allows researchers and clinicians to obtain high-density information with minimal assay time, sample volume, and cost. Such multiplexed analysis is accompanied by several challenges, including molecular encoding and the need to retain assay sensitivity, specificity, and reproducibility with the use of complex mixtures. There are two broad classes of technologies used for multiplexing: planar arrays (1-3) and suspension (particle-based) arrays (4-21), both of which have application-specific advantages. Numbers in parentheses refer to the references appended hereto, the contents of all of which are incorporated herein by reference. Planar arrays, such as DNA and protein microarrays, are best suited for applications requiring ultra-high-density analysis. In comparison, suspension arrays benefit from solution kinetics, ease of assay modification, higher sample throughput, and better quality control by batch synthesis (22). Although particle-based arrays have been used for high-density genotyping applications (23), they are most favorable over microarrays when detecting a modest number of targets over large populations or when rapid probe-set modification is desired. Whereas planar arrays rely strictly on positional encoding, suspension arrays have used a great number of encoding schemes that can be classified as spectrometric (4-11), graphical (12-16), electronic (17-19), or physical (20, 21).

Spectrometric encoding uses specific wavelengths of light or radiation [including fluorophores (4-7), chromophores (8), photonic structures (9), and Raman tags (10, 11)] to identify a species. Fluorescence-encoded microbeads (4-7) can be rapidly processed by using conventional flow cytometry [or on fiber-optic arrays (24)], making them a popular platform for multiplexing. However, there are several disadvantages of using multiple fluorescent signals as means of barcoding, including (i) the limited barcodes achievable (typically ~100) because of spectral overlap, (ii) the lack of portability for bulky flow cytometers, (iii) added cost with each fluorescent exciter and detector needed, and (iv) potential interference of encoding fluorescence with analyte-detection fluorescence. For these reasons, single-fluorescence methods exist that use graphical techniques to spatially embed barcodes on microcarriers.

Graphical barcodes rely on the patterning of optical elements on a microcarrier; some examples include striped rods (12, 13), ridged particles (14), and dot-patterned particles (14, 15). The chemistries used to fabricate such particles (metallic or photoresist) require additional coupling chemistries to conjugate biomolecules to the surface, and, in the case of striped rods, each metallic pattern needs to be generated one batch at a time. Typically, the patterns on these particles can only be distinguished if the fluorescence of the target signal is sufficiently high. Another graphical method for microcarrier encoding is the selective photobleaching of codes into fluorescent beads (16). In this method, both particle synthesis and decoding are time-consuming, making it an unlikely candidate for high-throughput analysis. A method that eliminates fluorescence altogether uses radio frequency memory tags (17-19). This approach is very powerful because it allows for nearly unlimited barcodes ($>10^{12}$) and decouples the barcoding scheme from analyte quantification (fluorescence), but the synthesis of any appreciable number (thousands or millions) of these electronic microchip-based carriers may prove to be expensive and slow. These and several other methods developed for multiplexed analysis have been thoroughly reviewed elsewhere (25, 26).

SUMMARY OF THE INVENTION

In one aspect, the invention is a method for making multifunctional particles including flowing a first monomer stream loaded with a fluorescent entity along a microfluidic channel. A second monomer stream loaded with a probe adjacent to the first monomer stream flows along the microfluidic channel. The two monomer streams are polymerized to synthesize particles having a fluorescent, graphically encoded region and a probe-loaded region. There may be more than two monomer streams if desired. In a preferred embodiment, the polymerizing step includes exposing the first and second monomer streams to ultraviolet light transmitted through a photomask to create the encoded region. The encoded region may include a plurality of open and closed coding elements. It is preferred that the coding elements be arranged in a two-dimensional grid. An exemplary grid includes 20 coding elements. The grid may also include at least one orientation indicator. In another preferred embodiment, the polymerizing step produces more than one probe-loaded region.

In a preferred embodiment, the ultraviolet light is focused by a microscope objective. A suitable material for the first and second monomer streams is poly(ethylene glycol) diacrylate. The first and second monomer streams preferably include a photoinitiator.

In yet another aspect, the invention is a multifunctional particle including a first graphically encoded region and a second region loaded with a probe.

In yet another aspect, the invention is a high-throughput screening system including multifunctional particles having a graphically encoded region and a probe-loaded region. A flow-focusing microfluidic device is provided to align and read the particles.

DESCRIPTION OF THE PREFERRED EMBODIMENTS

We introduce a technique that overcomes many of these multiplexing limitations. By exploiting laminar flows characteristic of microfluidics, we demonstrate the ability to generate multifunctional particles with distinct regions for analyte encoding and target capture (FIG. 1). In a typical experiment, we flowed two monomer streams (one loaded with a fluorescent dye and the other with an acrylate-modified probe) adjacently down a microfluidic channel and used a variation of continuous-flow lithography (27) to polymerize particles [with 30-ms bursts of ultraviolet (UV) light] across the streams (28). In this manner, particles with a fluorescent, graphically encoded region and a probe-loaded region can be synthesized in a single step. Each particle is an extruded two-dimensional (2D) shape (FIG. 1B) whose morphology is determined by a photomask that is inserted into the field-stop position of the microscope and whose chemistry is determined by the content of the coflowing monomer streams. The cross-linked polymer particles then flow down the channel [without sticking due to oxygen inhibition near the channel surfaces (27)], where they are collected in a reservoir. The particles can be rinsed of excess monomer and then used for biological assays.

Figure 1A:
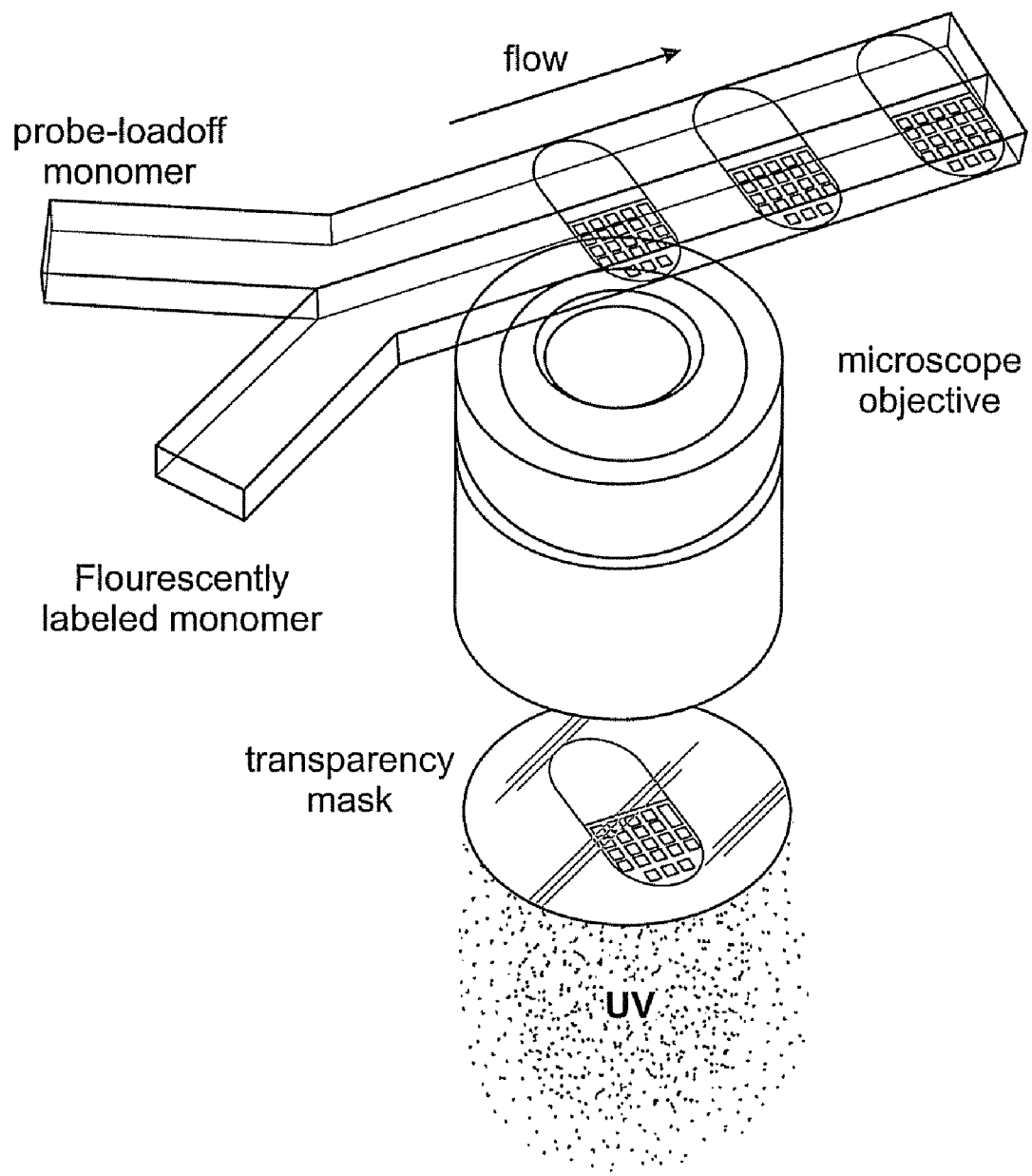
FIG. 1A is a schematic, perspective diagram of dot-coded particle synthesis showing polymerization across two adjacent laminar streams to make single-probe, half-fluorescent particles.
Figure 1B:
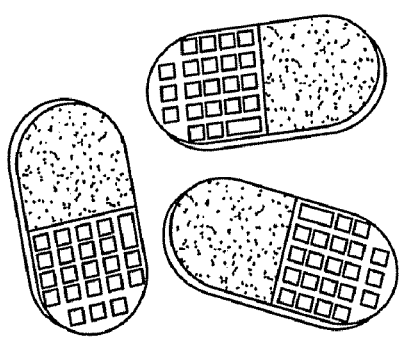
FIG. 1B is an illustration of the single-probe, half-fluorescent particles.
Figure 1C:
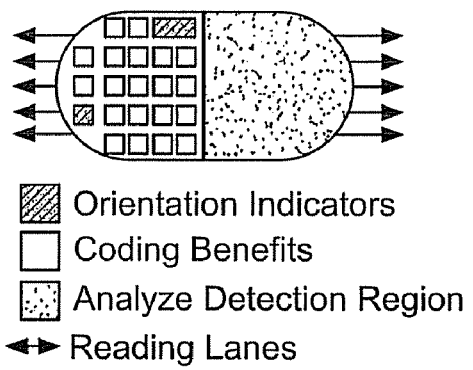
FIG. 1C is a diagrammatic representation of particle features for encoding and analyte detection.
Figure 1D:
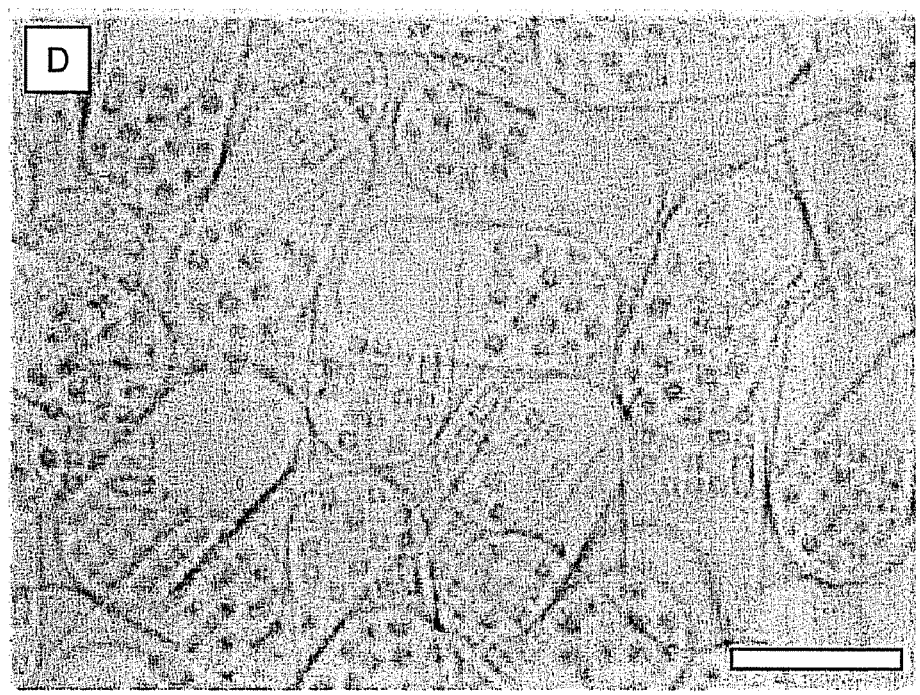
FIG. 1D is a differential interference contrast (DIC) image of particles generated by the technique shown in FIG. 1A.
Figure 1E:
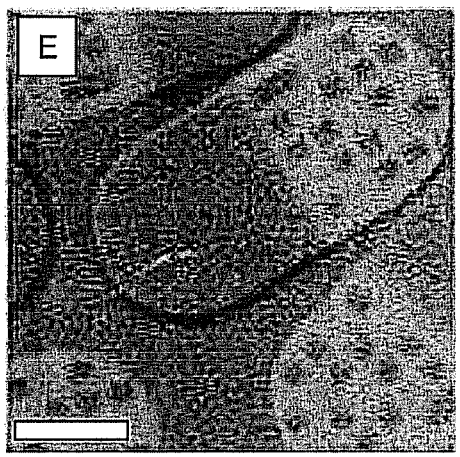
FIG. 1E is a photomicrograph of a single-probe particle.
Figure 1F:
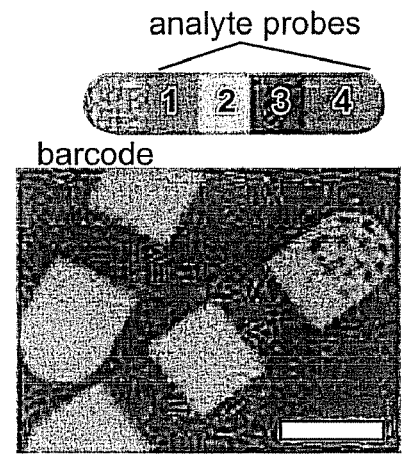
FIG. 1F is a photomicrograph showing a multi-probe particle.
Figure 1G:
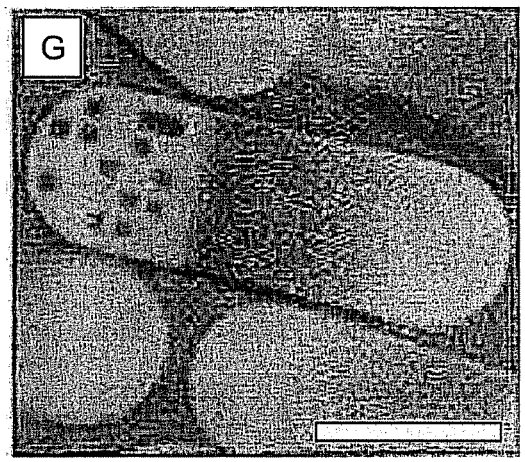
FIG. 1G is a photomicrograph showing probe-gradient encoded particles.
Figure 1H:
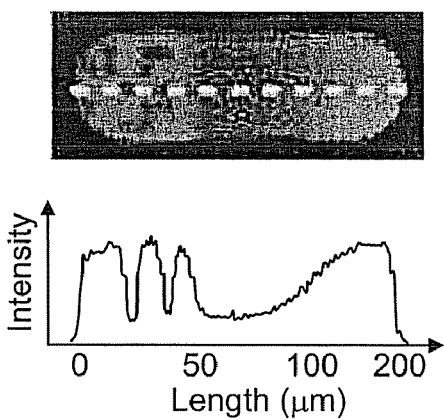
FIG. 1H is a plot of fluorescent intensity along the center line of a gradient particle.
Figure 2A:
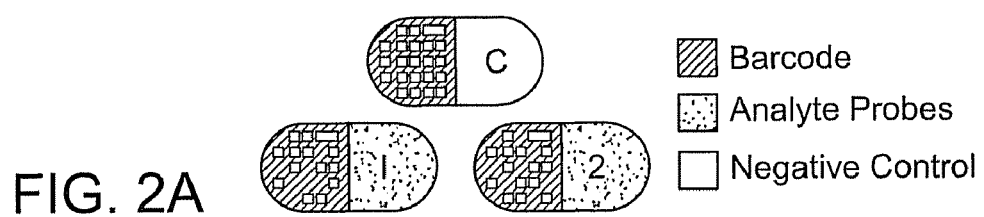
FIG. 2A-C illustrate multiplexed analysis using single-probe particles.
Figure 2B:
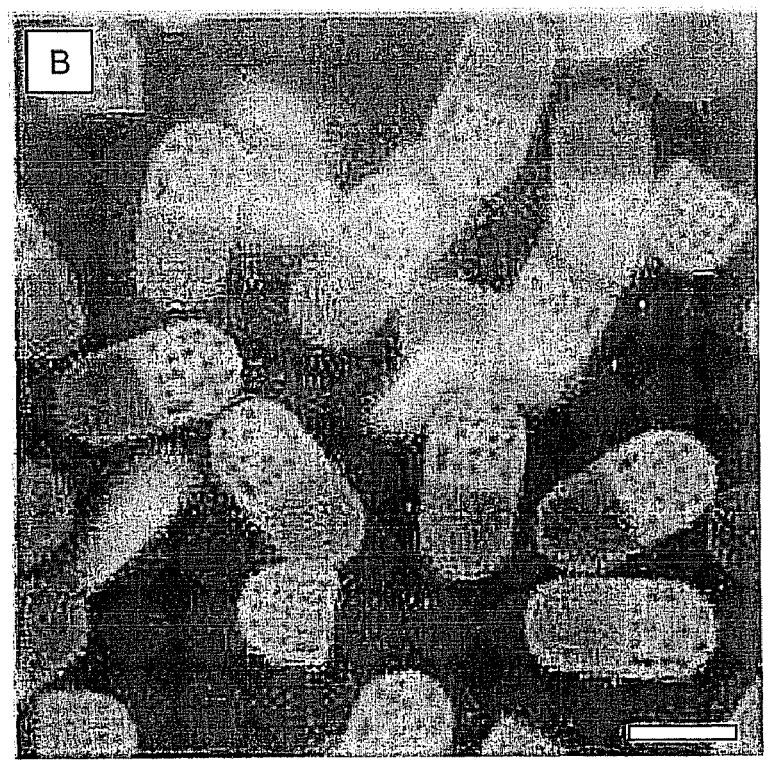
Figure 2C:
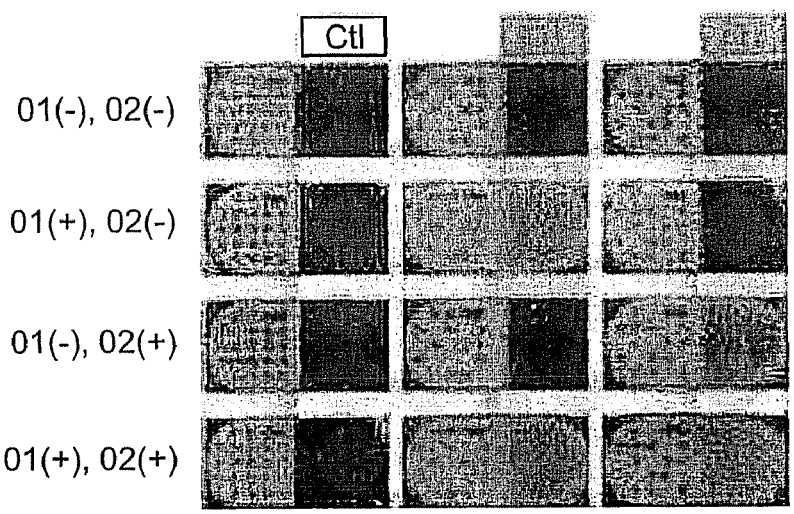
Figure 2D:
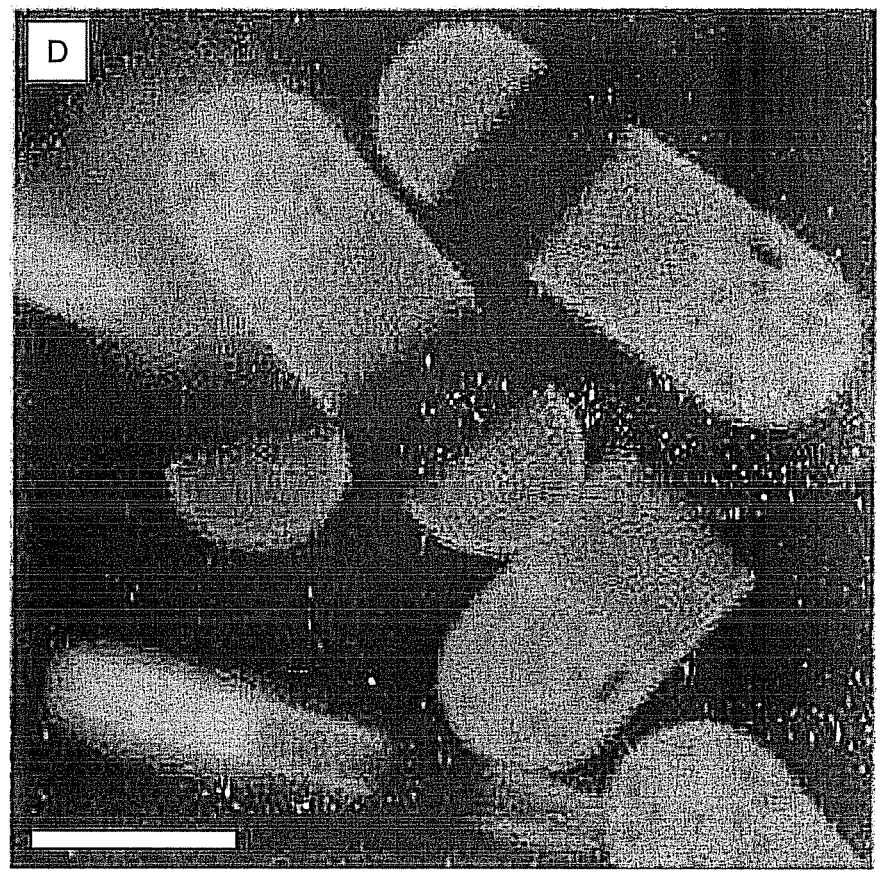
FIG. 2D-F illustrate multiplexed analysis using multi-probe encoded particles.
Figure 2E:
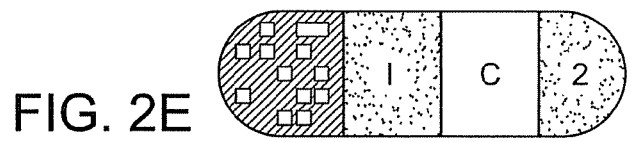
Figure 2F:
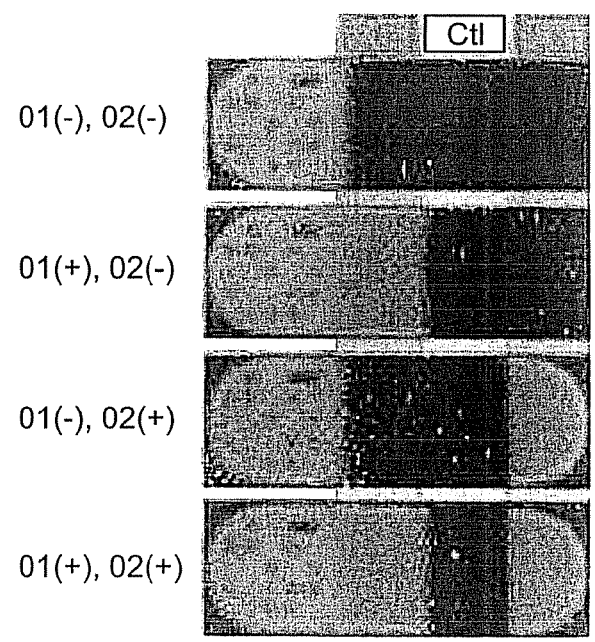

We used poly(ethylene glycol) (PEG) (well known as a bio-inert polymer) as the particle foundation to eliminate the need to "block" surfaces after probe conjugation and as a transparent material to allow transmission of fluorescent signal from both particle faces. These properties should enhance both specificity and sensitivity of analyte detection. Increasing analyte detection signal can be achieved by making the probes more accessible by increasing surface area in the probe region of the particle. Surface area can be increased by adding, for example, ridges or dimples. Signal can also be increased by increasing pore size. We used a simple dot-coding scheme to generate particles that can bear over a million ($2^{20}$) codes (FIG. 1C). Particles were designed to be "read" along five lanes down their length, with alignment indicators that were used to identify the code position and the read "direction" despite the particle orientation (FIG. 1C). The flat, long shape of the particles helps align them for scanning in a flow-through device. The spatial separation of various chemistries on the particles allows decoding and target detection to be achieved by using a single fluorophore.

To demonstrate the versatility of particle synthesis, we selectively labeled monomer streams with a fluorophore and used a variety of channel designs to generate particles bearing a single probe region, multiple probe regions, and probe-region gradients (FIG. 1, E to G). Multiprobe particles (FIG. 1F), made with the use of channels with several inlet streams, allow for a direct, single-particle comparison of several targets. Furthermore, probe gradients (FIG. 1G), made by simply allowing diffusion of the probe across streams in a long channel, are useful for broadening the detection range of an analyte when using a fixed detection sensitivity (when the signal can saturate). If magnetic nanoparticles are incorporated in a gradient, it may be possible to produce a temperature variation along particles when stimulated in an oscillating magnetic field (29).

A key feature of our method is the direct incorporation of probes into the encoded particles. This is accomplished by simply adding acrylate-modified biomolecules into the monomer solution. After polymerization, the probes are covalently coupled to the polymer network. This process is applicable for both oligonucleotide and protein probes (30-32). We demonstrate that the short bursts of UV used to synthesize probe-conjugated particles are not detrimental to the functionality of incorporated oligonucleotides. Previously, we showed similar results with bead-bound antibodies that were incorporated into polymer structures made from nearly identical monomer constituents (28, 33).

To demonstrate multiplexing capabilities, we used acrylate-modified oligonucleotide probes (which are commercially available) for DNA sequence detection (FIG. 2, A to C). We synthesized three batches of particles: one of which was loaded with 20-base pair (bp) oligonucleotide probe 1 (5'-ATA GCA GAT CAG CAG CCA GA-3'), another with probe 2 (5'-CAC TAT GCG CAG GTT CTC AT-3'), and a third with no probe, to serve as a control. Targets were fluorescently labeled oligonucleotides with complementary sequences to the two probes. We mixed the particles and incubated them for 10 min at room temperature in microwells containing either target 1 (at 1 µM), target 2 (at 1 µM), both targets (both at 0.5 µM), or no target (28). A positive target detection was indicated by probe-region fluorescence, which was more pronounced near the particle edges. This result suggested that targets were able to diffuse and hybridize several µm into the particle body (28). In each instance, the particles showed uniformity (28) with high specificity to the oligomers, exhibiting fluorescence only when the target was present (FIG. 2C).

To further demonstrate the power of our multiplexing scheme, we performed the same sequence detection assay with the use of particles with multiple adjacent functionalities (FIG. 2, D to F). In this manner, we were able to simultaneously assay for the two target sequences (with a negative control) on a single particle. Again, the assay was highly specific (FIG. 2F) and very uniform from particle to particle (FIG. 2D) (28). The interfaces between probes on the particles are very sharp, and thinner stripes could be used for even greater multiplexing capabilities.

Figure 3A:
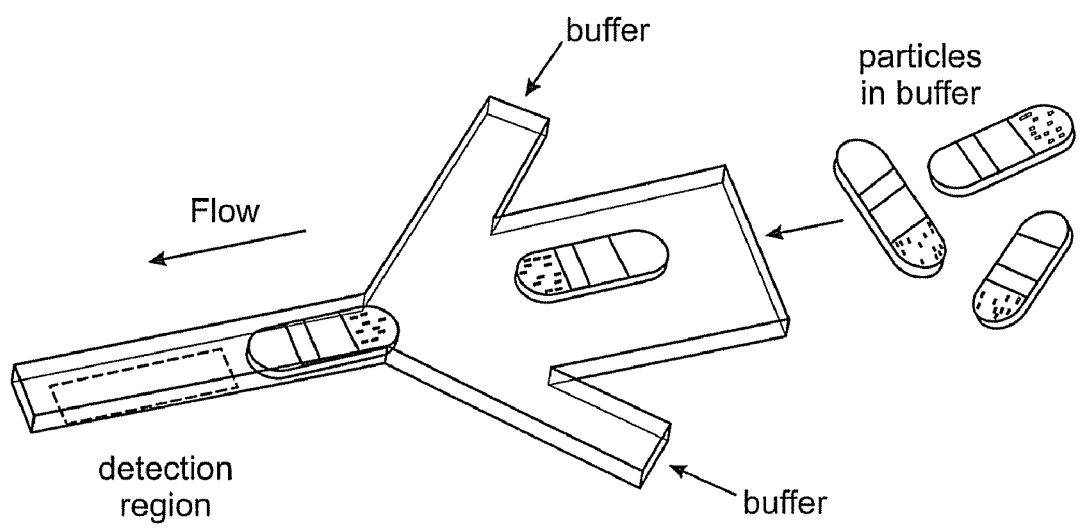
FIG. 3A is a perspective view of a schematic representation of a flow-focusing microfluidic device used to align and read particles after hybridization experiments.
Figure 3B:
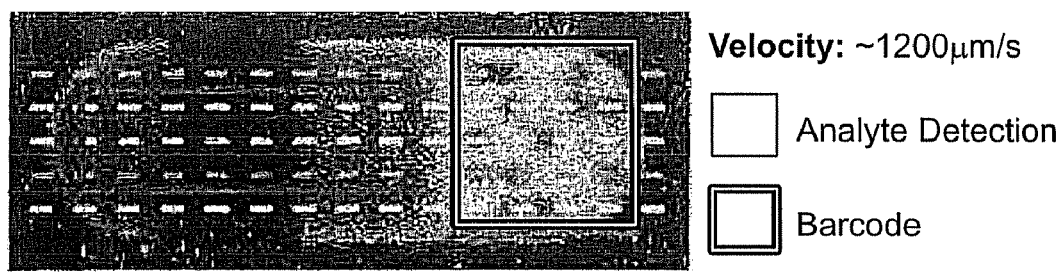
FIG. 3B is a typical image of a particle taken in a flow-through device shown in FIG. 3A.
Figure 3C:
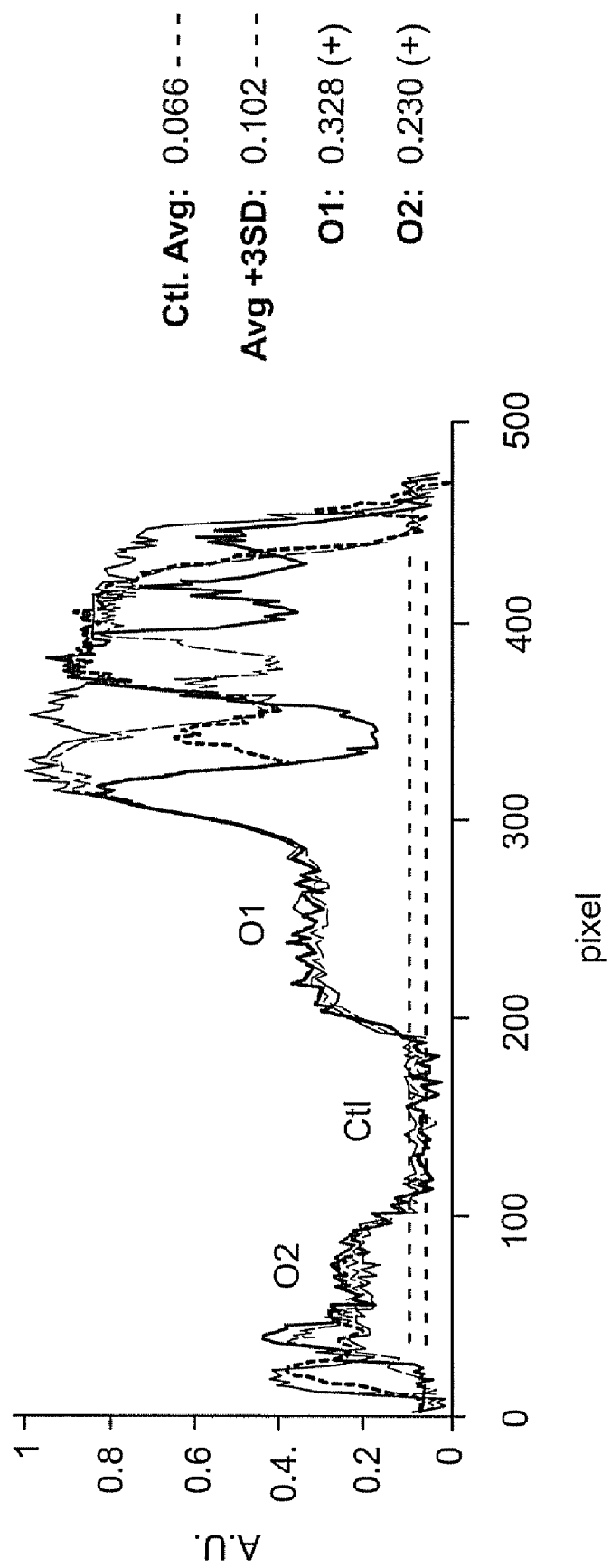
FIG. 3C is a graph showing scans of fluorescent intensity taken across the five lanes of the particle to reveal the code and to detect oligomer targets.

In order to prove that this method of multiplexed analysis is practical for high-throughput applications, we developed a simple scheme to scan particles in a flow-through device (FIG. 3). Multiprobe particles used in the hybridization experiment just described (FIG. 2, D to F) were flowed through a microfluidic channel and observed on an inverted fluorescence microscope (28). Particles were aligned by using flow-focusing and traveled down a channel only slightly larger than the particle width (FIG. 3A). We used a biofriendly surfactant (28) to ensure that the particles flowed smoothly down the channels without sticking. Images were taken at a designated detection region in the channel with an exposure of $\frac{1}{125}$ s as the particles passed the field of view (using a 20× objective). Image sequences were later analyzed to determine the particle code and quantify targets.

A representative particle image is shown (FIG. 3B) with corresponding intensity plots along the five particle "reading lanes." The code along each lane can be determined by analyzing the sharp dips and plateaus in the intensity plots. By using the control-region fluorescence, we defined a positive target detection as the control average intensity plus three standard deviations for each particle. We were able to accurately identify the presence of both oligonucleotide targets after only a short 10-minute incubation.

Figure 4A:
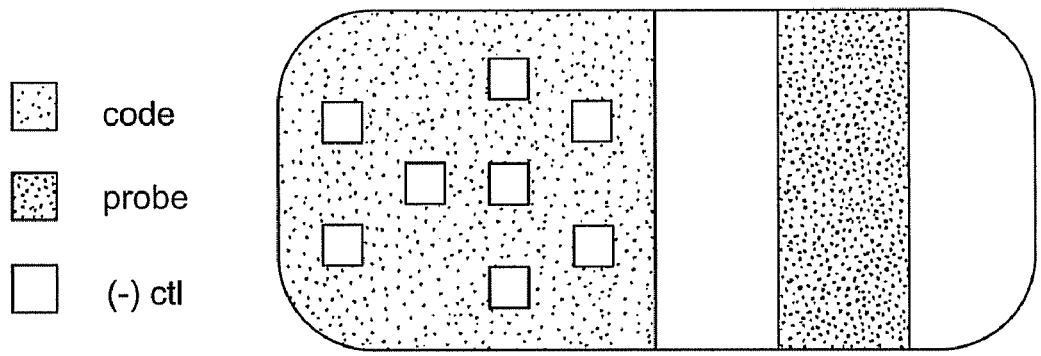
FIG. 4A is a schematic illustration of a particle including a one-dimensional encoding scheme.
Figure 4B:
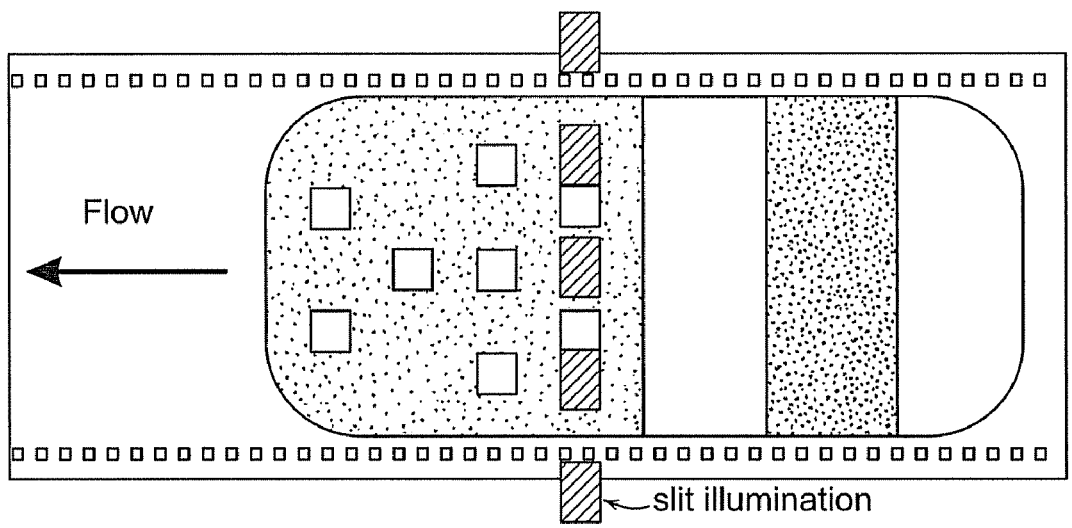
FIG. 4B is a schematic illustration showing slit illumination.
Figure 4C:
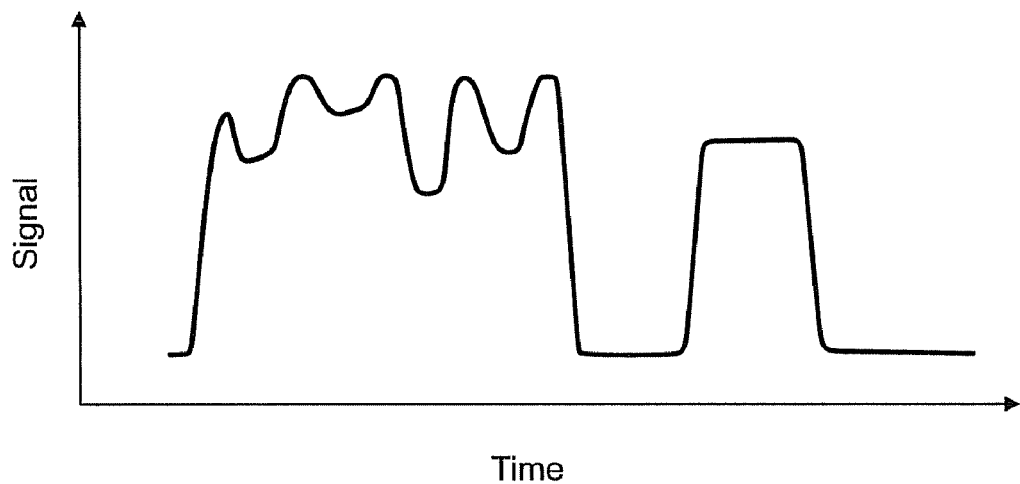
FIG. 4C is a graph of signal verses time comprising a series of valleys with varying depths in the acquired fluorescent signal.

Although the two-dimensional dot-pattern scheme discussed above is extremely powerful, it will require fairly sophisticated spatial detection. A potentially more practical, "one-dimensional" encoding scheme shown in FIG. 4 is capable of providing a more modest approximately 2,500 codes. As with the two-dimensional arrangement, the code will be a series of holes in a fluorescent background, but will be one-dimensional in that they provide a series of peaks and valleys when scanned across the entire width as shown in FIG. 4C. The embodiment in FIG. 4 is reproducable (preferably with a built-in "calibration") so as to ensure decoding accuracy and will not significantly affect particle integrity or required size.

In order to accurately and rapidly scan particles in this embodiment, we will use a detection scheme that provides rapid sampling with extremely sensitive light detection. Traditional microarray scanners and flow cytometers (and their microfluidic counterparts) utilize photomultiplier tube (PMT) modules for this purpose (37, 42, 43). These systems provide an extremely high sampling rate (~MHz) and extraordinary sensitivity, which makes them ideal for this application. These modules can be mounted directly to the camera port of a microscope and used seamlessly with the flow-focusing devices discussed above, given the appropriate illumination source and used with standard data acquisition software.

In a simple setup of this embodiment of the invention, the PMT module will collect all of the light relayed through the microscope port. Therefore, to obtain spatial information that will be used to decode the particles, it is preferred to illuminate only a thin-slit region perpendicular to the direction of particle movement. The slit size will be set by the encoding and probe feature sizes, which will likely be on the order of 10 µm. This resolution can be achieved by simply using a mask with our projection photolithography setup (27). More sophisticated illumination sources such as line-focused laser beams can also be used (44, 45). In another embodiment of the invention, broad illumination can be used with a slit-like filter placed in front of the PMT detector.

The throughput of our system is primarily determined by the detection scheme and the particle size. The particles synthesized for this study are relatively large compared with those in other flow-through methods, measuring 90 µm in width, ~30 µm in thickness, and 180 to 270 µm in length. Large size not only limits the throughput of a system but also increases the sample volume. However, the great particle-to-particle reproducibility we have demonstrated (28) will afford a much lower redundancy than is typical in flow-through systems, improving efficiency. By using conservative estimates, we found that our system should be capable of providing rapid, high-density analysis with a manageable sample volume (28) despite the seemingly large particle size.

In addition to being very reproducible, we have also shown that our system is very sensitive. With 30-min incubations, we can detect DNA oligomers comfortably at 500 attomoles without biotin-avidin-aided signal amplification (28). This leads us to believe that our system will be at least as sensitive as current, commercially available multiplexing technologies, with the added advantages of all-in-one particle synthesis, incorporation of multiple probes, low cost (28), virtually unlimited codes, and implementation using little more than a standard fluorescence microscope.

EXAMPLES

Materials and Methods

Materials

Particles synthesized in this work were made from monomer solutions based on poly(ethylene glycol) diacrylate (PEG-DA, Aldrich, $M_n$=700) with 2-hydroxy-2-methylpropiophenone photoinitiator (Aldrich). For hybridization experiments, we used monomer solutions of 2:1 PEG-DA:TE Buffer (10 mM Tris pH 8.0 (Rockland), 1 mM EDTA (OmniPur)) with 1-2.5% initiator and a DNA oligomer probe at a concentration of 50 µM. Oligomer probes (IDT) came modified with a reactive Acrydite group and 18-carbon spacer (Probe #1: 5'-Acrydite-C18-ATA GCA GAT CAG CAG CCA GA-3', Probe #2: 5'-Acrydite-C18-CAC TAT GCG CAG GTT CTC AT-3'). Encoded-region fluorescence was obtained by incorporating 0.005 wt % of methacryloxyethyl thiocarbamoyl rhodamine B (Polysciences) in the respective monomer solution with 1% blue food coloring to easily visualize the co-flowing streams using bright-field microscopy.

Microfluidic Devices

Microchannels were generated using standard procedures in soft lithography. Polydimethylsiloxane (PDMS) elastomer (Sylgard 184, Dow Corning) was cured on a silicon wafer bearing channel reliefs made using SU-8 photoresist (Microchem). Channels were designed such that multiple (2-7) 100 µm-wide inlet channels converged into a common, wider channel (200-500 µm wide). The channels (and reservoirs) were cut out with a scalpel, a hole was punched at each inlet, and the channels were sealed to PDMS-coated glass slides. Pipette tips (10 µl, Molecular BioProducts), connected with rubber tubing (Tygon) to a common pressure source (regulated by a pressure valve, Controlair Inc.), were each filled with 5 µl of polymer and inserted into the channel inlet ports. A three way solenoid valve (Burkert, operated manually) allowed for the oscillation between pressurized (~1 psi, high velocity) and ambient-pressure (no flow) states.

Photopolymerization Setup

Photomasks designed using AUTOCAD were printed with 20 000 dpi resolution at CAD/Art Services, Inc. (Brandon, Oreg.). The masks were inserted into the field-stop position of a Zeiss Axiovert 200 microscope, equipped with a 100 W HBO mercury lamp and wide-excitation ultraviolet (UV) filter set (11000v2:UV, Chroma). A computer-driven shutter system (UniBlitz) was in place to provide the desired pulses of UV excitation. Particles were polymerized across adjacent streams in a microfluidic channel with 30-50 ms bursts of UV excitation. Using the three way valve to control flowrate, particles were polymerized in a no-flow state and immediately flushed down the channel in a pressurized state—providing clean interfaces between adjacent streams with high resolution of particle features. Visual alignment for polymerization was achieved using a CCD camera (KPM 1A, Hitachi) with NIH Image software.

Particle Recovery

Particles were collected in a reservoir after polymerization where they were cleaned of unreacted monomer. The particles were rinsed several times with TE buffer, then with PEG-DA monomer, and again with TE buffer until all residual fluorescence was gone. After each rinse, the particles were allowed to settle to the bottom of the reservoir and excess rinsing solution was pipetted from the top. Particles were typically used immediately for hybridization experiments but were occasionally used after being stored for several days in a dark environment, showing no loss of functionality.

Oligomer Hybridization

Particles were pipetted into separate PDMS reservoirs for each hybridization experiment. Complementary target DNA oligomers modified with a Cy3 fluorophore (IDT) were suspended at concentration of 1 μM in hybridization buffer (TE buffer with 0.2M NaCl (Mallinckrodt) and 0.5% sodium dodecyl sulfate (SDS, Invitrogen)). Solutions of target oligomer were pipetted into the appropriate reservoirs and the particles were incubated for 10 min at room temperature. The particles were then rinsed several times with TE buffer and visualized using an orange longpass filter set (XF101-2, Omega), which is compatible with both rhodamine B and Cy3 fluorophores. Still images were captured using a Nikon D200 digital camera.

Particle Reading

Flow-focusing microfluidic channels were plasma-sealed at the inlets on a PDMS-coated glass slide. Prior to particle reading, the channel was flushed with "read buffer" (TE with 25% PEG-DA and 0.5% Tween 20) for 5 min. Multi-probe particles used in hybridization experiments were resuspended in read buffer and pipetted into the channel reservoir. The pressure system described previously was used with a column of water to pull a vacuum on the channel and induce fluid flow. Particles were observed flowing through a 100 μm channel constriction with a Zeiss Axiovert 200 microscope and imaged with an exposure of 1/250 sec under fluorescence with a CCD camera (Hitachi KPM1A). Movies were taken using NIH image at 10 frames per second—particle velocities were calculated and intensity profiles were taken along the 5 "lanes" of each particle. The average and standard deviation of the intensity along the control region of a particle were taken. A positive reading for an oligomer target was defined as the average plus three standard deviations of the negative control signal.

Investigation of Particle Composition

Probe Concentration

Figure 5:
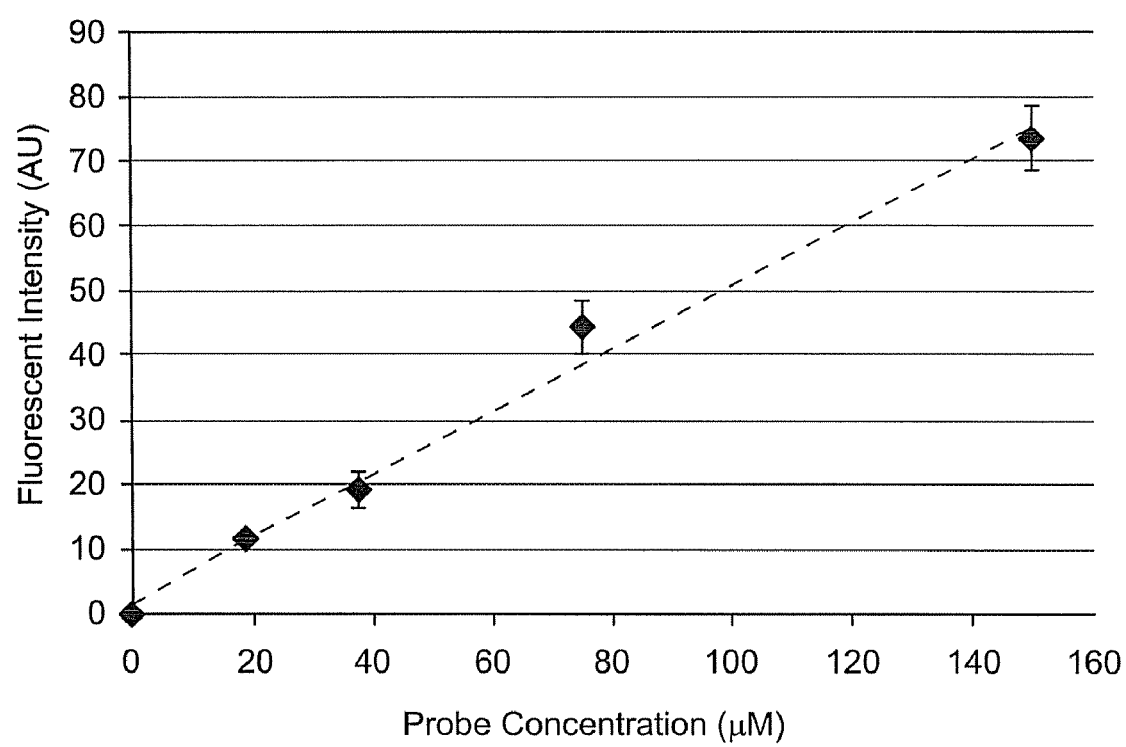
FIG. 5 is a graph showing fluorescent intensity of particles with varying probe concentrations.

We used serial dilution of an oligomer probe in monomer to determine the effect of concentration on signal detection. We synthesized particles with probe concentrations of 150, 75, 37.5, and 18.75 μM. Control particles (0 μM probe) were used to determine the background intensity ($I_b$). The particles were incubated for 30 min with a fluorescent-labelled target at 1 μM, rinsed, and imaged to determine fluorescent intensity ($I_p$). The fluorescent signal is reported in arbitrary units (AUs) taken as the difference $I_P$–$I_b$. The results are shown in FIG. 5. The error bars on the graph represent the standard deviation in each measurement, with an average coefficient of variation (COV) of 9%.

As can be seen, the intensity increases linearly with probe concentration. This finding is expected when considering the binding of two complementary oligomers—at equilibrium, the relationship is given as:

where T=target, P=probe, and TP=double stranded complex. At equilibrium, the concentrations of the species can be characterized by a dissociation constant, $K_d$, such that:

$$K_d = \frac{[P][T]}{[PT]}$$

If $[T]_o \gg [P]_o$ as is the case in our experiment, then $[T] \approx [T]_o$. Using this, and the relationship $[P]=[P]_o-[PT]$, we obtain:

$$[PT] = \frac{[P]_o[T]_o}{K_d + [T]_o}$$

Thus, for a given initial concentration of target, we can expect the signal (which is proportional to [PT]) to be linear with respect to the probe concentration. Although we could obtain a much higher signal with increased probe concentration, we chose to incorporate 50 μM probe for proof of principle experiments—this concentration gave sufficient signal for target detection with minimal usage of oligomer.

Monomers

We investigated the use of several polymers for barcoded particles, including poly(ethylene glycol) diacrylate of three chain lengths ($M_n$=200, 400, 700) and also a blend of acrylamide with PEG-DA as crosslinker. The characteristics investigated when selecting a polymer blend were (1) fast polymerization kinetics, (2) low background fluorescence before hybridization, and (3) a strong fluorescence signal after hybridization. All solutions we made consisted of monomer (pure or at 2:1 with TE buffer), 2.5% photoinitiator, and DNA oligomer at 50 μM. Particles were made using 30 ms UV exposure with a 20× objective.

We found that hybridization signals were significantly higher when TE buffer was included in the monomer blend. This is consistent with our previous work (33), in which we discovered that bead-bound proteins incorporated in polymerized PEG hydrogels lost functionality in the absence of buffer. We found that PEG-DA ($M_n$, =700) had significantly faster reaction kinetics than the other monomers and also showed significantly less background signal. The final monomer solution we chose for hybridization experiments was a 2:1 blend of PEG-DA:TE with 1-2.5% photoinitiator.

Particle Characterization

Polydispersity

It is very important that the particles being used for quantitative biomolecule analysis be consistent both morphologically and functionally. We have already shown that particles synthesized using continuous-flow lithography have a very low coefficient of variation (<2%) with respect to physical size (27). We also performed experiments to investigate the variation of fluorescent signal for particles used in a hybridization study.

The fluorescent intensity of particles used in a hybridization study gives evidence of the "functional" polydispersity of the particles. However, this measure is not only dependent on the particles, but also on the hybridization experiment itself—the numbers we present should be a conservative estimate. We found the COV of fluorescent signal to range from 6-10% when incubating with target at concentrations of 1 µM-10 nM and increase to ~15-30% for lower concentrations (down to 10 pM).

Active Probe Concentration

Figure 6:
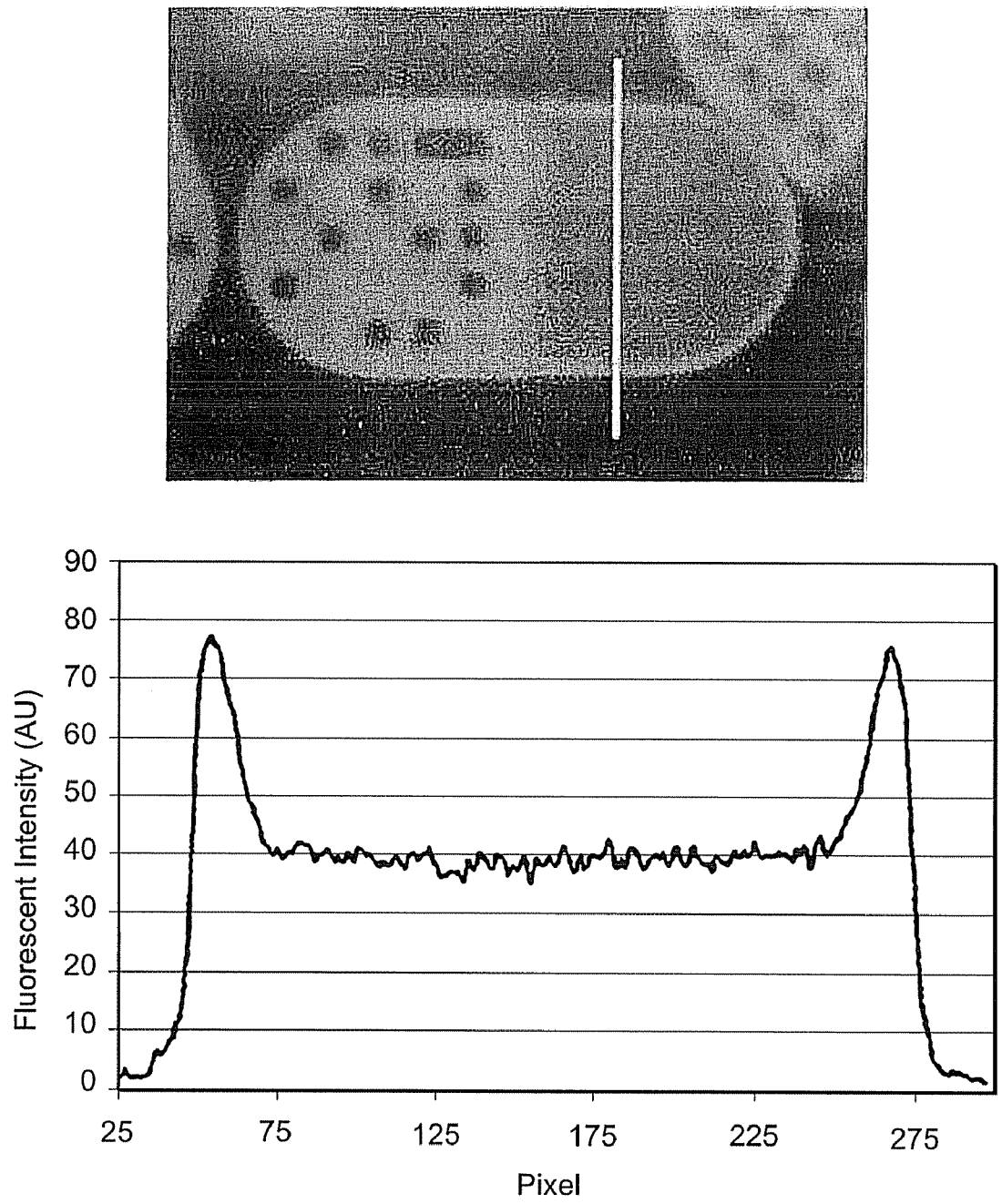
FIG. 6 is a plot of fluorescent intensity across a particle section after target hybridization. The white line on the particle image indicates the region that was scanned.

In order to calculate the concentration of probe on the particle surfaces, we used the concentration of probe incorporated into our monomer solution (50 µM) with an estimate of the depth to which oligomers can diffuse into particles and react. Shown in FIG. 6 is a typical particle used in a hybridization study with a scan of fluorescent intensity across its sensing region.

As can be seen, the particle shows a significantly higher signal at the edges of its sensing region—the coded region does not show this characteristic because the fluorescent dye incorporated has been homogeneously distributed throughout. We assumed that this "edge" signal was proportional to the amount of oligomer bound to the 30 µm-thick edge of the particle. The intensity in the interior of the particle was almost exactly ½ that of the edge for the several particles we investigated. Assuming that all surfaces are similar, we deduced that the active binding thickness in the interior of the particle must be $$30\,\mu m \times \frac{80\,AD}{40\,AD} = 15\,\mu m,$$

or ~7.5 µm per face. As validation, we can see that the width of the high-intensity region at each particle edge is ~20 pixels=8 µm. Physically, this can be explained by the pore size. The polymerization of particles occurs most rapidly at the center (where oxygen must diffuse the furthest and the concentration of free radicals is the highest) and slower at the particle surface. Therefore, we can assume that the particles are more tightly crosslinked at the center than near the surfaces, providing larger pores into which short oligomers can diffuse and react with complementary probes. Based on the work of others, the PEG polymer we used should have a pore size of ~10 Å when completely crosslinked (34, 35).

Using the probe concentration of 50 µM (in monomer), with an active thickness of 7.5 µm per face and a 50% incorporation efficiency, we estimated the effective surface concentration to be:

$$\frac{50\,\mu M}{7.5\,\mu m} \times 50\% \simeq 10^5 \frac{\text{molecules}}{\mu m^2} \text{ per face}$$

Because the particles are transparent, the fluorescence of both faces should give a projected probe concentration of $$2 \times 10^5 \frac{\text{molecules}}{\mu m^2}.$$

This is a similar "surface" concentration to those reported by others (36). As mentioned previously, we can incorporate a substantially greater amount of probe into our particles to make the surface concentration much higher, thus increasing the sensitivity of our system.

Estimation of Throughput

Recently, microfluidic-based flow cytometers have been developed with integrated photomultiplier tubes to achieve a very high throughput. The fluid velocities in these systems can be on the order of 10 m/s (similar to conventional flow cytometers) while detection is carried out at a high sample rate of 5 MHz, allowing a particle read rate of 17,000/sec (37). We use this as a basis to estimate the throughput we can achieve with our system when incorporating more sophisticated sensing schemes. Conservatively, we estimated a flow velocity of 1 m/s and a spacing of 10 particle lengths between particles (each 200 µm in length). Thus, we can calculate a throughput of $$THROUGHPUT = 1\frac{\text{meter}}{\text{sec}} \times \frac{1}{2,200}\frac{\text{particles}}{\mu m} \approx 450\frac{\text{particles}}{\text{sec}}$$

Although this "particle/sec" throughput seems lower than that typically seen in flow cytometry, we discuss why on a "target/sec" basis, the technology should provide a sufficient throughput for high-density analysis.

We have shown that our system exhibits excellent particle-to-particle reproducibility (as discussed above). Enzyme-linked immunosorbant assays (ELISAs), which are considered to be the gold standard in sensing, show similar precision (38) to our technology and are typically done only in duplicate. This level of redundancy is significantly lower than seen in flow cytometry-based assays. We will assume for estimation purposes that our assays can be performed in triplicate to yield accurate information. With a redundancy of 3, our "target/sec" throughput becomes $$THROUGHPUT = 450\frac{\text{particles}}{\text{sec}} \times \frac{1}{3}\frac{\text{target}}{\text{particles}} \approx 150\frac{\text{targets}}{\text{sec}}.$$

Two simple modifications that will provide an even higher throughput are (1) reduction of particle size, and (2) incorporation of several probes on a single particle. We have demonstrated in our lab the ability to produce particles with features on the order of ~1 µm, so it is well within reason to consider the production of encoded particles that are half-sized in each dimension. This would increase the number of particles/volume by a factor of 8. Furthermore, if the particles have 3 functionalities (two probes and a control as in FIG. 6), this increases the throughput by another factor of 2. Using these arguments, we can calculate some expected throughputs:

TABLE 1

Estimation of throughput and particle volume for tests done in triplicate (each probe appears on three particles). "Normal" particle size is ~ 100 × 200 × 30 µm, while "half" size is ~ 50 × 100 × 15 µm. Particle volume is based on $10^6$ targets tested, which for single and two-probe particles corresponds to $3 \times 10^6$ and $1.67 \times 10^6$ total particles, respectively.

| Particle Size | Probes/Particle | Throughput ($\frac{\text{targets}}{\text{sec}}$) | Particle Volume ($\frac{\mu L}{10^6 \text{targets}}$) |
|---|---|---|---|
| Normal | 1 | 150 | 1,800 |
| Half | 1 | 300 | 225 |
| Normal | 2 | 300 | 900 |
| Half | 2 | 600 | 113 |

From this simple analysis, it seems reasonable to analyze one million targets in less than one hour when using reduced-size and/or multi-probe particles. This analysis also highlights the importance of particle size in terms of volume—reduced-size particles will likely be necessary for high-density analysis.

Limits of Detection

Figure 7:
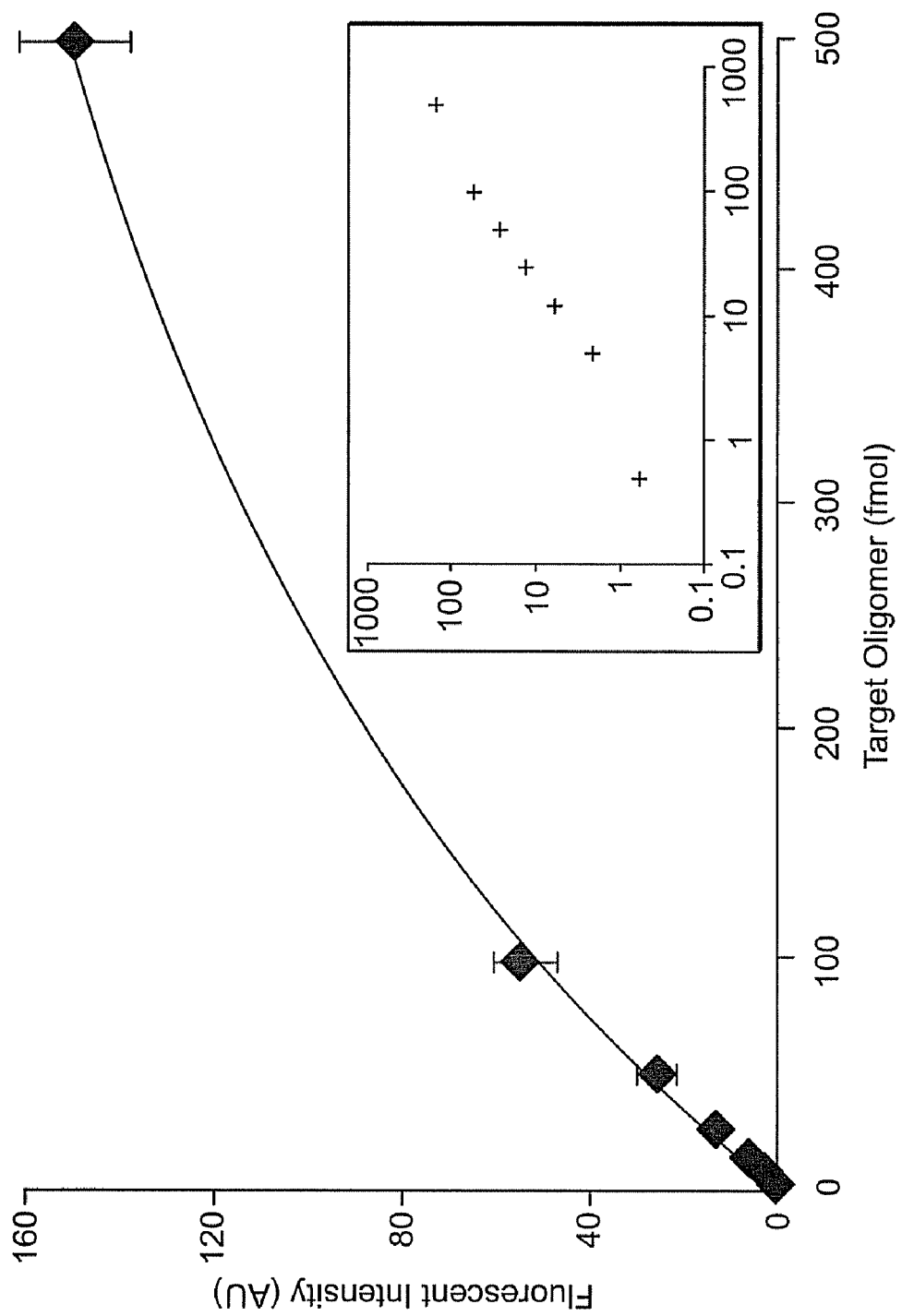
FIG. 7 is a plot of hybridization signal (fluorescent intensity) of particles incubated at varying target concentrations.

We hybridized particles with fluorescent target at concentrations spanning over several orders of magnitude in order to determine a suitable range of detection. Samples of particles from a common batch (with 50 μM probe incorporated) were incubated with 50 μl of target solution for 30 min at room temperature on a vortex mixer—target concentrations ranged from 10 nM-10 pM corresponding to 500 fmol-500 amol ($10^{-18}$ moles) of oligomer. After hybridization, the particles were rinsed and imaged under fluorescence for detection with an EB-CCD camera (C7-190-20, Hamamatsu) mounted to our microscope. Because the system had an 8-bit limited dynamic range, it was necessary to use three different sensitivity settings to accommodate the broad range in fluorescent signal. As such, two of the particle batches were imaged at two of the three sensitivity settings so the signals could be normalized and plotted on a common scale. The results of the detection study are shown in FIG. 7.

As can be seen, this plot is not linear as was the case with varying probe concentrations (FIG. 5). This is because at lower target concentrations, the amount of target is no longer much greater than the amount of probe ($[T]_o >> [P]_o$), and the approximation that $[T]=[T]_o$ can no longer be made. Additionally, it is known that the time taken to reach equilibrium increases with decreasing target (39)—the incubation time used in this experiment (30 min) was not likely sufficient for this to occur.

We found the assay to be quite sensitive, detecting oligomer comfortably at the lowest amount tested (500 amole) without biotin/avidin-based signal amplification. This finding suggests that our system has a comparable sensitivity to the current state of the art multiplexing systems including Affymetrix (40) and Luminex (41). Furthermore, we showed previously that we can increase the sensitivity of the assay by incorporating higher probe concentrations of probe into the particles.

Cost of Materials

At standard non-bulk pricing, the raw material cost to produce 1 million single-probe particles similar to those presented in the manuscript is only $4.28 ($0.14 without DNA probe) as outlined below:

TABLE 2

Estimation of raw material cost to produce $10^6$ particles (~100 × 200 × 300 μm) with DNA oligomer probe incorporated at a concentration of 50 μM.

| Component | Unit Price | Price per $10^6$ Particles |
|---|---|---|
| PEG Monomer | $ 50/500 ml | $ 0.06 |
| Photoinitiator | $ 80/250 ml | <$ 0.01 |
| Fluorescent Dye | $ 560/1 g | $ 0.08 |
| 20 bp DNA Probe | & 276/1 μmole | $ 4.14 |
| | | Total: $ 4.28 |

As described earlier, it would be reasonable to make particles half-sized in each dimension, which would reduce particle volume and cost by a factor of 8 (to only $0.54 per 106 particles). It is also important to note that very little sample is wasted due to the low-volume microfluidic processing.

The microchannels used for particle synthesis and flow-through reading are of simple design and can be generated very economically. A single 4" wafer (<$100), generated using standard SU-8 lithography, can easily bear over 10 channels and be molded from many times (we assume 10 times for subsequent calculations). In addition, each device may be used several times (we will use 5). Therefore, using very conservative estimates, the device cost would be:

TABLE 3

Estimated cost of microdevices used for particle synthesis and flow-through reading. It was assumed that master wafers have 10 channels and can be molded 10 times, and that each device could be used 5 times before being discarded.

| Component | Unit Price | Price per Device |
|---|---|---|
| Fabrication of Master | $ 100/100 channels | $ 1.00 |
| PDMS | $ 0.10/g | $ 0.25 |
| Microscope Slide | $ 100/400 | $ 0.25 |
| | | Total: $ 1.50 |
| | | Price per use: $ 0.30 |

The material cost for a single multiplex experiment with a million particles would be <$5.00 ($4.28 for the particles and $0.60 for one "synthesis" and one "read" channel). This estimate does not include the buffer used in particle reading, which consists of inexpensive materials and would be negligible in the overall cost.

REFERENCES

1. D. Gershon, *Nature* 416, 885 (2002).
2. S. P. Fodor et al., *Nature* 364, 555 (1993).
3. G. MacBeath, S. L Schreiber, *Science* 289, 1760 (2000).
4. R. J. Fulton, R. L. McDade, P. L. Smith, L. J. Kienker, J. R. Kettman Jr., *Clin. Chem.* 43, 1749 (1997).
5. B. J. Battersby et al., *J. Am. Chem. Soc.* 122, 2138 (2000).
6. H. Xu et al., *Nucleic Acids Res.* 31, e43 (2003).
7. M. Han, X. Gao, J. Z. Su, S, Nie, *Nat. Biotechnol.* 19, 631 (2001).
8. X. W. Zhao et al., *Chem. Mater.* 18, 2443 (2006).
9. F. Cunin et al., *Nat. Mater.* 1, 39 (2002).
10. X. Su et al., *Nano Lett.* 5, 49 (2005).
11. H. Fenniri, S. Chun, L. Ding, Y. Zyrianov, K. Hallenga, *J. Am. Chem. Soc.* 125, 10546 (2003).
12. S. R. Nicewarner-Peña et al., *Science* 294, 137 (2001).
13. M. Y. Sha et al., *Anal. Bioanal. Chem.* 384, 658 (2006).
14. M. Evans, C. Sewter, E. Hill, *Assay Drug Dev. Technol.* 1, 199 (2003).
15. Z. L. Zhi, Y. Morita, Q. Hasan, E. Tamiya, *Anal Chem.* 75, 4125 (2003).
16. K. Braeckmans et al., *Nat. Mater.* 2, 169 (2003).
17. E. J. Moran et al., *J. Am. Chem. Soc.* 117, 10787 (1995).
18. K. C. Nicolaou, X. Y. Xiao, Z. Parandoosh, A. Senyei, M. P. Nova, *Angew. Chem. Int. Ed.* 34, 2289 (1995).
19. R. F. Service, *Science* 270, 577 (1995).
20. T. M. McHugh, R. C. Miner, L H. Logan, D. P. Stites, *J. Clin. Microbial* 26, 1957 (1988).
21. A. R. Vaino, K. D. Janda, *Proc. Natl. Acad. Sc.* U.S.A. 97, 7692 (2000).
22. J. P. Nolan, L. A. Sklar, *Trends Biotechnol.* 20, 9 (2002).
23. J. B. Fan, M. S. Chee, K. L Gunderson, *Nat. Rev. Genet.* 7, 632 (2006).
24. J. A. Ferguson, F. J. Steemers, D. R. Walt, *Anal Chem.* 72, 5618 (2000).
25. N. H. Finkel, X. Lou, C. Wang, L. He, *Anal Chem.* 76, 352A (2004).
26. K. Braeckmans, S. C. D: Smedt, M. Leblans, R. Pauwels, J. Demeester, *Nat. Rev. Drug Discov.* 1, 447 (2002).
27. D. Dendukuri, D. C. Pregibon, J. Collins, T. A. Hatton, P. S. Doyle, *Nat. Mater.* 5, 365 (2006).

28. Materials and methods are available as supporting material on *Science* Online.
29. R. Hergt et al., *IEEE Trans. Magn.* 34, 3745 (1998).
30. A. Y. Rubina et al., *Biotechniques* 34, 1008 (2003).
31. A. V. Vasiliskov et al., *Biotechniques* 27, 592 (1999).
32. F. N. Rehman et al., *Nucleic Acids Res.* 27, 649 (1999).
33. D. C. Pregibon, M. Toner, P. S. Doyle, *Langmuir* 22, 5122 (2006).
34. M. B. Mellott, K. Searcy, M. V. Pishko, *Biomaterials* 22, 929 (2001).
35. G. M. Cruise, D. S. Scharp, J. A. Hubbell, *Biomaterials* 19, 1287 (1998).
36. Y. Kohara, H. Noda, K. Okano, H. Kambara, *Nucleic Acids Res.* 30, e87 (2002).
37. C. Simonnet, A. Groisman, *Anal. Chem.* 78, 5653 (2006).
38. W. de Jager, G. T. Rijkers, *Methods* 38, 294 (2006).
39. P. W. Stevens, M. R. Henry, D. M. Kelso, *Nucleic Acids Res.* 27, 1719 (1999).
40. R. A. Irizarry, Z. Wu, H. A. Jaffee, *Bioinformatics* 22, 789 (2006).
41. S. A. Dunbar, C. A. V. Zee, K. G. Oliver, K. L. Karem, J. W. Jacobson, *J. Microbiol. Methods* 53, 245 (2003).
42. Wang et al., *Lab Chip,* 4, 2004.
43. McClain et al., *Anal. Chem.,* 73, 2001.
44. Eyal and Quake, *Electrophoresis,* 23, 2003.
45. Sinclair et al., *App. Optics,* 43, 2004.

---

What is claimed is:

1. A method for making multifunctional particles comprising:
    flowing a first monomer stream along a microfluidic channel;
    flowing a second monomer stream loaded with at least one probe along the microfluidic channel; and
    polymerizing the first and second monomer streams to synthesize particles having a graphically encoded region and a probe-loaded region, wherein the probe-loaded region is distinct from the graphically encoded region and wherein the graphically encoded region comprises spatially patterned features,
    wherein the polymerizing step includes exposing the monomer streams to light transmitted through a photomask such that the particle shape is defined in at least one dimension by the shape of the illuminating light.

2. The method of claim 1, wherein the probe includes DNA or RNA.

3. The method of claim 1, wherein the probe includes protein.

4. The method of claim 1, wherein the probe includes an inert species to serve as a negative control.

5. The method of claim 1, wherein the spatially patterned features of the graphically encoded region include a plurality of open and closed coding elements.

6. The method of claim 5, wherein the coding elements are arranged in a two-dimensional grid.

7. The method of claim 6, wherein the grid includes 20 coding elements.

8. The method of claim 5, wherein the graphically encoded region further includes at least one orientation indicator.

9. The method of claim 5, wherein the coding elements have non-uniform shapes or sizes.

10. The method of claim 1, wherein the polymerizing step produces more than one probe-loaded region.

11. The method of claim 1, wherein the polymerizing step produces more than one graphically encoded region.

12. The method of claim 1, wherein the light is focused by a microscope objective.

13. The method of claim 1, wherein the first and second monomer streams comprise poly(ethylene glycol) diacrylate.

14. The method of claim 13, wherein the first and second monomer streams comprise a photoinitiator.

15. The method of claim 1, wherein the particles comprise ridges or dimples in the probe-loaded region.

16. The method of claim 1, where the first monomer stream is adjacent to the second monomer stream.

17. The method of claim 1, wherein the first monomer stream further comprises a fluorescent entity.

18. The method of claim 1, wherein the polymerizing step comprises a photopolymerization step.

19. The method of claim 18, wherein the photopolymerization step comprises ultraviolet (UV) excitation.

20. The method of claim 1, wherein the probe-loaded region comprises multiple probes.

21. The method of claim 1, wherein the particles are detectable by flow-through reading.

22. The method of claim 21, wherein the method further comprises a step of characterizing the particles by flow-through reading.

23. The method of claim 1, wherein the graphically encoded region is made from more than one encoding stream.

24. The method of claim 23, wherein the graphically encoded region is loaded with one or more fluorescent entities.

25. The method of claim 1, wherein the probe comprises a linking chemical entity.

26. The method of claim 1, wherein the spatially patterned features allow decoding of the graphically encoded region.

* * * * *